(12) United States Patent
Kawabata et al.

(10) Patent No.: US 8,110,603 B2
(45) Date of Patent: Feb. 7, 2012

(54) ORGANIC PERACID POLYMER COMPOSITION AND PROCESS FOR PRODUCING THE SAME

(75) Inventors: Yasunari Kawabata, Katsushika-ku (JP); Yasushi Hiramatsu, Katsushika-ku (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 847 days.

(21) Appl. No.: 11/989,429

(22) PCT Filed: Jul. 18, 2006

(86) PCT No.: PCT/JP2006/314169
§ 371 (c)(1),
(2), (4) Date: Jan. 25, 2008

(87) PCT Pub. No.: WO2007/013324
PCT Pub. Date: Feb. 1, 2007

(65) Prior Publication Data
US 2010/0143491 A1 Jun. 10, 2010

(30) Foreign Application Priority Data
Jul. 27, 2005 (JP) ................. 2005-217224

(51) Int. Cl.
*A01N 37/00* (2006.01)
*A61K 31/19* (2006.01)
(52) U.S. Cl. ........ 514/557; 424/703; 424/605; 510/376; 514/574
(58) Field of Classification Search ........................ None
See application file for complete search history.

(56) References Cited

U.S. PATENT DOCUMENTS

| 5,804,669 | A | 9/1998 | Tropsch et al. |
| 5,922,814 | A * | 7/1999 | Tropsch et al. ............ 525/326.9 |
| 6,254,801 | B1 * | 7/2001 | Reinold et al. ........... 252/186.23 |
| 6,518,307 | B2 * | 2/2003 | McKenzie et al. ............ 514/557 |

FOREIGN PATENT DOCUMENTS

| JP | 10-7724 | 1/1998 |
| JP | 2005-519090 | 6/2005 |
| WO | 94/20600 | 9/1994 |
| WO | 03/073849 | 9/2003 |

OTHER PUBLICATIONS

International Search Report issued Aug. 15, 2006 in the International (PCT) Application PCT/JP2006/314169 of which the present application is the U.S. National Stage.

* cited by examiner

*Primary Examiner* — Patricia A Duffy
*Assistant Examiner* — Garen Gotfredson
(74) *Attorney, Agent, or Firm* — Wenderoth, Lind & Ponack, L.L.P.

(57) ABSTRACT

It is intended to provide an organic peracid polymer composition which is stable, odorless and has sufficient water solubility and is suitably used as a bactericide, a bleaching agent and a cleaning agent. By mixing and dissolving an organic acid polymer, hydrogen peroxide and an inorganic acid and maintaining the mixture for a period ranging from 1 hour to 1 month at a temperature ranging from 10 to 80° C., the organic peracid polymer-containing composition containing an organic peracid polymer (2 to 50% by weight) and, in some cases, the hydrogen peroxide (2 to 50% by weight) and the inorganic acid (0.1 to 10% by weight) is obtained.

18 Claims, No Drawings

ORGANIC PERACID POLYMER COMPOSITION AND PROCESS FOR PRODUCING THE SAME

TECHNICAL FIELD

The present invention relates to an organic peracid polymer-containing composition excellent in disinfectant, bleaching and cleaning effects.

BACKGROUND ART

Conventionally, various peroxides have been used for disinfectant, bleaching and cleaning compositions. Among them, performic acid, peracetic acid, perpropionic acid, perbutyric acid, permalonic acid, persuccinic acid, perglutaric acid, peradipic acid, pertartaric acid, percitric acid, perbenzoic acid and perphthalic acid are known as an organic peracid. These peracids are useful in applications of disinfectant agents, bleaching agents, cleaning agents and epoxidizing agents. However, these organic peracids are not necessarily satisfactory in terms of stability, odor, water solubility and the like.

Patent Document 1 discloses a mildew-removing agent composition containing peroxide and an organic polymer. The peroxide used here has such a defect that it does not have sufficient disinfectant, bleaching and cleaning properties.
Patent Document 1:
Jpn. Pat. Appln. Laid-Open Publication No. S61-158907

DISCLOSURE OF THE INVENTION

Problems to be Solved by the Invention

The problem to be solved by the present invention is to obtain an organic peracid polymer-containing composition having excellent disinfectant and bleaching capabilities, having satisfactory stability, being less in odor and having sufficient water solubility.

Means for Solving the Problems

As a result of the intensive studies to solve the above problems, the present inventors have found that a composition containing an organic peracid polymer obtained by converting at least part of the carboxyl groups in the structural units of an organic acid polymer into peroxycarboxyl groups is excellent in disinfectant, bleaching and cleaning capabilities, excellent in stability, being less in odor and has sufficient water solubility.

Moreover, the present inventors have found that, when producing a composition containing the organic peracid polymer, conversion of carboxyl groups in an organic acid polymer into peroxycarboxyl groups by hydrogen peroxide can proceed efficiently by means of using an inorganic acid as an acid catalyst in addition to the mixture of the organic acid polymer and hydrogen peroxide.

That is, the present invention relates to a disinfectant, bleaching and cleaning composition and a process for producing the same shown in the following (1) to (21).
(1) A disinfectant, bleaching and cleaning composition characterized in that it comprises an organic peracid polymer obtained by converting at least part of carboxyl groups in the structural units of an organic acid polymer into peroxycarboxyl groups.
(2) The composition according to (1), wherein the converting ratio of carboxyl groups into peroxycarboxyl groups in said organic peracid polymer is not less than 5%.
(3) The composition according to (1) or (2), wherein the molecular weight of said organic peracid polymer is 500 to 100,000.
(4) The composition according to any one of (1) to (3), wherein said organic peracid polymer is at least one selected from the group consisting of perpolyacrylic acid, perpolymethacrylic acid, perpolymaleic acid, peracrylic acid copolymer, permethacrylic acid copolymer, permaleic acid copolymer and salts thereof.
(5) The composition according to any one of (1) to (4), wherein the concentration of said organic peracid polymer is 2 to 50% by weight.
(6) The composition according to any one of (1) to (5), which further comprises hydrogen peroxide and an inorganic acid.
(7) The composition according to (6), wherein said inorganic acid is at least one selected from the group consisting of sulfuric acid, orthophosphoric acid and pyrophosphoric acid.
(8) The composition according to (1) to (7), which further comprises a stabilizer.
(9) The composition according to (8), wherein said stabilizer is at least one selected from the group consisting of orthophosphoric acid, 1-hydroxyethane-1,1-bis(phosphonic acid) or a salt thereof, pyrophosphate, hexametaphosphate and dipicolinic acid.
(10) A process for producing an organic peracid polymer-containing composition comprising an organic peracid polymer obtained by converting at least part of carboxyl groups in the structural units of an organic acid polymer into peroxycarboxyl groups, which comprises at least a mixing step of mixing the following components (i) to (iv):
(i) an organic acid polymer having carboxyl groups in its structural units,
(ii) hydrogen peroxide,
(iii) an inorganic acid and
(iv) water.
(11) The process according to (10), wherein the mixture is maintained for a period ranging from 1 hour to 1 month in said mixing step.
(12) The process according to (10) or (11), wherein carboxyl groups in the structural units of said organic acid polymer are converted into peroxycarboxyl groups with the converting ratio of not less than 5% in said mixing step.
(13) The process according to any one of (10) to (12), wherein the molecular weight of said organic acid polymer is 500 to 100,000.
(14) The process according to (10) to (13), wherein said organic acid polymer is at least one selected from the group consisting of polyacrylic acid, polymethacrylic acid, polymaleic acid, acrylic acid copolymer, methacrylic acid copolymer, maleic acid copolymer and salts thereof.
(15) The process according to any one of (10) to (14), wherein the mixing ratio of said components (i) to (iv) is that organic acid polymer; 3 to 60% by weight, hydrogen peroxide; 2 to 60% by weight, an inorganic acid; 0.1 to 10% by weight, and water; 20 to 90% by weight.
(16) The process according to any one of (10) to (15), wherein said inorganic acid is at least one selected from the group consisting of sulfuric acid, orthophosphoric acid and pyrophosphoric acid.
(17) The process according to (10) to (16), wherein a stabilizer is further mixed in said mixing step.
(18) The process according to (17), wherein said stabilizer is at least one selected from the group consisting of orthophosphoric acid, 1-hydroxyethane-1,1-bis(phosphonic acid) or a salt thereof, pyrophosphate, hexametaphosphate and dipicolinic acid.

(19) The process according to any one of (10) to (18), which further comprises a diluting step wherein a diluent is added following to said mixing step.

(20) An organic peracid polymer-containing composition produced by the process according to any one of (10) to (19), which comprises an organic peracid polymer; 2 to 50% by weight, hydrogen peroxide; 2 to 50% by weight, and an inorganic acid; 0.1 to 10% by weight.

(21) An organic peracid polymer-containing diluted composition obtained by diluting the organic peracid polymer-containing composition according to (20).

The above-mentioned Patent Document 1 discloses a mildew-removing agent composition containing peroxide and an organic polymer. However, it does not mention anything about an organic peracid polymer. In addition, even if hydrogen peroxide is used as a peroxide and an organic acid polymer is used as an organic polymer in the Patent Document 1, an extremely small amount of an organic peracid polymer is produced in the case not comprising an inorganic acid as an acid catalyst, and performances as an organic peracid polymer can not be exhibited.

Advantages of the Invention

The composition of the present invention containing an organic peracid polymer as an active component, has excellent disinfectant, bleaching and cleaning capabilities compared with a composition containing peroxides such as organic peracids used for conventional disinfectant, bleaching and cleaning agents or a mere mixture of an organic acid polymer and hydrogen peroxide. It exhibits higher disinfectant, bleaching and cleaning effects even compared with those having the same effective oxygen concentration. Further, the composition of the present invention is characterized in that, since the organic peracid polymer is stable and not easily decomposed, the disinfectant, bleaching and cleaning effects thereof can not be defected under the long-term storage. In addition, since the organic peracid polymer used in the present invention has less odor and has sufficient water solubility, it is easy to use the composition in the case of using it by diluting. Therefore, it is excellent in practicability and it can be comfortably applied not only for industrial use but also for domestic use.

In addition, according to the process of the present invention, since an inorganic acid is used as an acid catalyst, peroxidation (equilibrium reaction) of carboxyl groups in an organic acid polymer with hydrogen peroxide proceed quickly to the direction of producing peroxycarboxyl groups and reaches to the equilibrium state under the high concentration of peroxycarboxyl groups. Therefore, it is possible to produce a product having a high concentration of organic peracid polymer using a solution containing a high concentration of an organic acid polymer. Thus, a composition containing a sufficient amount of an organic peracid polymer can be obtained.

Further, since the above-mentioned equilibrium reaction is difficult to proceed under the low concentration of an organic acid polymer, it is not easy to efficiently obtain a composition having a low concentration of an organic peracid polymer with relatively high water content. However, according to the process of the present invention, it is possible to produce a composition having sufficient amount of an organic peracid polymer by processing the above-mentioned equilibrium reaction efficiently under the high concentration. Therefore, by diluting the organic peracid polymer composition thus produced, an organic peracid polymer composition having any concentration can be obtained efficiently.

BEST MODE FOR CARRYING OUT THE INVENTION

1. Disinfectant, Bleaching and Cleaning Composition:

The disinfectant, bleaching and cleaning composition of the present invention comprises an organic peracid polymer as an active component.

(1) Organic Peracid Polymer:

The organic peracid polymer in the present invention is a polymer having a structure wherein at least part of carboxyl groups in the structural units of an organic acid polymer are converted into peroxycarboxyl groups.

Examples thereof include perpolyacrylic acid, perpolymethacrylic acid, perpolymaleic acid, peracrylic acid copolymer, permethacrylic acid copolymer, permaleic acid copolymer and salts thereof. Examples of the salts include sodium salts and potassium salts. The organic peracid polymer of the present invention is at least one kind selected from the group consisting of the above compounds, among which only one kind may be used or two kinds or more may be used together.

The lower limit of the converting ratio of carboxyl groups into peroxycarboxyl groups is preferably 5%, more preferably 7%, further preferably 10%. The higher limit thereof is preferably 90%, more preferably 70%, further preferably 50%. The one wherein the converting ratio is too low can not exhibit disinfectant, bleaching and cleaning effects sufficiently as an organic peracid. The one wherein the converting ratio is too high may have difficulty in manufacture.

The molecular weight of the organic peracid polymer is preferably 500 to 100,000, more preferably 2,000 to 20,000. When the molecular weight of the organic peracid polymer is too low, disinfectant, bleaching and cleaning effects as an organic peracid may not be exhibited sufficiently. The one wherein the molecular weight thereof is too high may have difficulty in manufacture.

The concentration of the organic peracid polymer in the disinfectant, bleaching and cleaning composition of the present invention is preferably 2 to 50% by weight, more preferably 2 to 15% by weight. That is, it is possible for the disinfectant, bleaching and cleaning composition of the present invention to contain relatively high concentration of an organic peracid polymer. The composition having too high concentration of an organic peracid polymer may have difficulty in manufacture. When the concentration of an organic peracid polymer is too low, disinfectant, bleaching and cleaning effects as an organic peracid may not be exhibited sufficiently. However, since the disinfectant, bleaching and cleaning composition of the present invention is excellent in disinfectant, bleaching and cleaning capabilities of the organic peracid polymer, it is possible to exhibit excellent disinfectant, bleaching and cleaning effects sufficiently even if the composition is diluted. Therefore, the above-mentioned concentration of the organic peracid polymer should not be particularly limited.

The concentration of the organic peracid polymer of the present invention can be determined by the following mathematical formula (1). In addition, the converting ratio (%) of carboxyl groups into peroxycarboxyl groups can be determined by the mathematical formula (1) (see the mathematical formula (2)).

(Mathematical Formula 1)

$$P = Q \times R/100 \times (C+16)/C \quad (1)$$

$$R = (P/Q) \times C/(C+16) \times 100 \quad (2)$$

In the above mathematical formula (1), P represents the concentration of the organic peracid polymer (% by weight), Q represents the concentration of the organic acid polymer before peroxidation (% by weight), R represents the converting ratio of carboxyl groups into peroxycarboxyl groups (%), and C represents the molecular weight of the organic acid polymer per carboxyl group respectively.

(2) Other Components:

<Hydrogen Peroxide>

The composition of the present invention may comprise hydrogen peroxide other than the above-mentioned organic peracid polymer. The composition of the present invention usually contains hydrogen peroxide which is used for converting carboxyl groups in the structural units of an organic acid polymer into peroxycarboxyl groups at the step of producing said composition. Since hydrogen peroxide itself has disinfectant, bleaching and cleaning capabilities, it contributes not only to disinfectant, bleaching and cleaning effects of the composition as a whole but also to generation and maintenance (stability in its solution) of sufficient amount of an organic peracid polymer by equilibrium reaction with an organic acid polymer. Therefore, by the combination of an organic peracid polymer and hydrogen peroxide, disinfectant, bleaching and cleaning effects of the composition of the present invention can be improved.

The concentration of hydrogen peroxide in the composition of the present invention is preferably 2 to 50% by weight, more preferably 5 to 30% by weight. When the concentration of hydrogen peroxide is too low, the amount of the organic peracid polymer produced by equilibrium reaction with the organic acid polymer may not be satisfactory and disinfectant, bleaching and cleaning effects of the present invention may not be exhibited sufficiently. On the other hand, even if the concentration of hydrogen peroxide is too high, the above effects can not be improved, and a problem with security may occur.

<Inorganic Acid>

An inorganic acid can enhance the effect of increasing the concentration of an organic peracid polymer in the composition of the present invention. The reason for this seems that the conversion of carboxyl groups into peroxycarboxyl groups is promoted since dissociation of carboxyl groups in the organic acid polymer is restrained under the influence of the inorganic acid. That is, under the absence of an inorganic acid, it may be difficult to obtain a composition having such high concentration of an organic peracid polymer as the present invention.

Suitable inorganic acids include one selected from the group consisting of sulfuric acid, orthophosphoric acid and pyrophosphoric acid. Only one kind thereof can be used independently, or two kinds or more can be used together. The concentration of an inorganic acid is 0.1 to 10% by weight, preferably 0.3 to 5% by weight. When the concentration of an inorganic acid is too low, the above-mentioned effects can not be achieved efficiently. Even if the concentration is too high, the above-mentioned effects can not be improved.

<Stabilizer>

It is preferable that the composition of the present invention comprises a stabilizer. By adding a stabilizer into the composition, the stability of an organic peracid polymer and hydrogen peroxide can be improved. Any stabilizers for peracids can be used as the stabilizer. Especially, it is preferable to select one from the group consisting of orthophosphoric acid, 1-hydroxyethane-1,1-bis(phosphonic acid) or salts thereof, pyrophosphate, hexametaphosphate and dipicolinic acid. Examples of the salts include a sodium salt and a potassium salt, and more preferably, a sodium salt. Only one kind of them can be used independently, or two kinds or more can be used together.

The concentration of the stabilizer is preferably 0.01 to 5% by weight, more preferably 0.02 to 3% by weight. Though the stabilizer can be used if necessary, sufficient effect of stabilization of peracid may not be achieved when the concentration of the stabilizer is too low. On the other hand, even if the concentration of the stabilizer is too high, the stabilization effect can not be improved.

<Other Components>

The disinfectant, bleaching and cleaning composition of the present invention can further contain commonly-used additives used for disinfectant, bleaching and cleaning agents and the like such as a surfactant, a thickening agent, a flavoring agent and a coloring agent appropriately if necessary. In the disinfectant, bleaching and cleaning composition of the present invention, a residual component other than an organic peracid polymer, hydrogen peroxide, an inorganic acid and additives such as a stabilizer added if necessary is mainly water.

The pH of the disinfectant, bleaching and cleaning composition of the present invention is not higher than 3, preferably not higher than pH 1. When pH is higher than 3, a composition having high concentration of an organic peracid polymer may not be obtained. If the composition of the present invention comprises an inorganic acid, pH usually becomes not higher than 3.

The disinfectant, bleaching and cleaning composition of the present invention can be used by diluting to any concentration of an organic peracid polymer. Examples of diluents include water and an alcoholic aqueous solution. Though dilution rate is not particularly limited, it is preferable to dilute 1.1 to 10,000 times, more preferably 1.1 to 1000 times.

2. Process for Producing an Organic Peracid Polymer Composition:

Secondly, a process for producing an organic peracid polymer-containing composition of the present invention will be described. The process of the present invention is a process for producing a composition comprising an organic peracid polymer wherein at least part of carboxyl groups in the structural units of an organic acid polymer are converted into peroxycarboxyl groups, which comprises at least a mixing step of mixing the following components (i) to (iv):

(i) an organic acid polymer having carboxyl groups in its structural units, (ii) hydrogen peroxide, (iii) an inorganic acid and (iv) water.

(1) Mixing Step

In the above-mentioned mixing step, an organic acid polymer, hydrogen peroxide, an inorganic acid and water are mixed and dissolved and then the mixed solution thus obtained is maintained for preferably 1 hour to 1 month, more preferably 4 hours to 20 days. Though the temperature for mixing and dissolving in the mixing step is not particularly limited, 10 to 80° C. is preferable, 20 to 70° C. is more preferable.

In the mixing step, when the above-mentioned components are mixed and dissolved, carboxyl groups in the organic acid polymer are reacted with hydrogen peroxide to convert into peroxycarboxyl groups gradually. This reaction of an organic acid polymer with hydrogen peroxide proceeds as equilibrium reaction of the organic peracid polymer, hydrogen peroxide and the organic acid polymer. The converting ratio reaches maximum after about 1 hour to 1 month, and then it becomes nearly constant. The converting ratio becomes higher by raising the concentration of hydrogen peroxide. That is, as the concentration of an organic acid polymer and hydrogen peroxide increases, the concentration of an organic peracid polymer generated increases.

<Organic Acid Polymer>

The organic acid polymer to be used for the process of the present invention is not particularly limited as long as it is a polymer having carboxyl groups in its structural units. Examples of the polymer include polyacrylic acid, polymethacrylic acid, polymaleic acid, acrylic acid copolymer, methacrylic acid copolymer, maleic acid copolymer and salts thereof. Only one kind thereof can be used independently, or two kinds or more can be used together.

The molecular weight of said organic acid polymer is preferably 500 to 100,000, more preferably 2000 to 20,000. When the molecular weight of the organic acid polymer is too low, an organic peracid polymer having sufficiently high disinfectant, bleaching and cleaning effects may not be obtained. When the molecular weight thereof is too high, manufacture of the organic peracid polymer-containing composition may have difficulty.

The charged amount (usage amount or mixing rate) of the organic acid polymer is preferably 3 to 60% by weight, more preferably 5 to 40% by weight based upon the total charged amount of the charged materials (or mixed materials). When the usage amount of the organic acid polymer is too small, the concentration of the organic peracid polymer in the organic peracid polymer-containing composition thus obtained may decrease and the disinfectant, bleaching and cleaning effects of said organic peracid polymer-containing composition may not be exhibited sufficiently. On the other hand, even if the usage amount of the organic acid polymer is too large, the concentration of the organic peracid polymer does not necessarily increase according to the usage amount.

<Hydrogen Peroxide>

As hydrogen peroxide to be used in the process of the present invention, same hydrogen peroxide as one comprised in the above-mentioned disinfectant, bleaching and cleaning composition of the present invention may be used. Moreover, it is preferable to use hydrogen peroxide which is previously purified in order to improve long-term storage stability. The methods for purification include a method of contacting with ion exchange resins or chelating resins.

Since hydrogen peroxide itself has disinfectant, bleaching and cleaning capabilities, it contributes not only to disinfectant, bleaching and cleaning effects of the organic peracid polymer-containing composition obtained as a whole but also to generating a sufficient amount of an organic peracid polymer by equilibrium reaction with an organic acid polymer and maintaining thereof. Therefore, by combining and mixing the organic acid polymer and hydrogen peroxide, the composition containing high concentration of the organic peracid polymer can be obtained.

The charged amount of hydrogen peroxide is preferably 2 to 60% by weight, more preferably 5 to 40% by weight. When the usage amount of hydrogen peroxide is too small, the amount of an organic peracid polymer generated by equilibrium reaction with the organic acid polymer may not be sufficient, and the disinfectant, bleaching and cleaning effects of the present invention may not be exhibited efficiently. On the other hand, even if the concentration of hydrogen peroxide is too high, the concentration of the organic peracid polymer cannot necessarily increase according to the usage amount.

<Inorganic Acid>

An inorganic acid can improve the effect of increasing the concentration of an organic peracid polymer in the organic peracid polymer-containing composition obtained by the process of the present invention. The reason for this seems that the conversion of carboxyl groups into peroxycarboxyl groups can be promoted since dissociation of carboxyl groups in the organic acid polymer is restrained under the influence of the inorganic acid. That is, under the absence of an inorganic acid, it may be difficult to obtain a composition containing high concentration of an organic peracid polymer.

As an inorganic acid to be used in the process of the present invention, same inorganic acid as one comprised in the above-mentioned disinfectant, bleaching and cleaning composition of the present invention may be used. That is, one selected from the group consisting of sulfuric acid, orthophosphoric acid and pyrophosphoric acid can be used as an inorganic acid. Only one kind thereof can be used independently, or two kinds or more can be used together.

The charged amount of the inorganic acid is preferably 0.1 to 10% by weight, more preferably 0.3 to 5% by weight. When the usage amount of the inorganic acid is too low, an organic peracid polymer may not be produced in a sufficient concentration. On the other hand, even if the usage amount of the inorganic acid is too high, the concentration of an organic peracid polymer can not necessarily be increased.

<Stabilizer>

In the process of the present invention, it is possible to use a stabilizer if necessary. By adding a stabilizer, the stability of an organic peracid polymer to be generated and hydrogen peroxide can be improved. Any stabilizers for peracids can be used as the stabilizer. It is preferable to select one from the group consisting of orthophosphoric acid, 1-hydroxyethane-1,1-bis(phosphonic acid) or salts thereof, pyrophosphate, hexametaphosphate and dipicolinic acid, which are same as the one used for the above-mentioned disinfectant, bleaching and cleaning composition of the present invention. Examples of the salts include a sodium salt and a potassium salt, more preferably a sodium salt. Only one kind of them can be used independently, or two kinds or more can be used together.

In the case of adding a stabilizer, it can be added in the composition already containing an organic peracid polymer, hydrogen peroxide and an inorganic acid after generating the organic peracid polymer. However, it is preferable that a stabilizer is added together with an organic acid polymer, hydrogen peroxide and an inorganic acid when mixing them in the above-mentioned mixing step.

<Other Components>

Among the starting materials of the producing process of the present invention, a residual component other than an organic acid polymer, hydrogen peroxide, an inorganic acid and additives to be added if necessary is mainly water. The amount of water is preferably 20 to 90% by weight, more preferably 30 to 70% by weight. In the producing process of the present invention, commonly-used additives used for usual disinfectant, bleaching and cleaning agents and the like, such as a surfactant, a thickening agent, a flavoring agent and a coloring agent, can further be added appropriately.

In the present invention, an organic peracid polymer is produced by equilibrium reaction of an organic acid polymer with hydrogen peroxide. Therefore, it is preferable to use an organic acid polymer and hydrogen peroxide at the ratio of an organic acid polymer:hydrogen peroxide=10-90:90-10. In addition, the charged amount of an inorganic acid functioning as an acid catalyst is preferably 0.5 to 30% based upon the charged amount of an organic acid polymer.

In the above-mentioned mixing step, the lower limit of the converting ratio of carboxyl groups in the organic acid polymer into peroxycarboxyl groups is preferably 5%, more preferably 7%, further preferably 10%. The higher limit thereof is preferably 90%, more preferably 70%, further preferably 50%. According to the producing process of the present invention, it is possible to produce an organic peracid polymer in high concentration by using an inorganic acid as a catalyst for equilibrium reaction of an organic acid polymer with hydrogen peroxide. When the converting ratio is too low, disinfectant, bleaching and cleaning effects of thus obtained organic peracid polymer-containing composition may not be exhibited sufficiently. The composition wherein the converting ratio is too high may be difficult to produce.

(2) Diluting Step:

The producing process of the present invention can comprise a diluting step of further adding a diluent after the above-mentioned mixing step. Examples of diluents include water and an alcoholic aqueous solution. Though dilution rate is not particularly limited, it is preferable to dilute 1.1 to 10,000 times, more preferably 1.1 to 1000 times.

In the present invention, firstly a mixed solution containing a high concentration of an organic acid polymer and hydroxy peroxide is prepared. Then, a composition containing a high concentration of an organic peracid polymer is obtained by equilibrium reaction of the organic acid polymer with hydrogen peroxide. Subsequently, by diluting the composition thus obtained, a composition having any concentration of an organic peracid polymer can be produced efficiently. If it is intended to obtain the organic peracid polymer-containing composition by using a mixed solution containing a low concentration of an organic acid polymer from the beginning, it may be difficult to produce the composition having any concentration of an organic peracid polymer efficiently, since the equilibrium reaction of the organic acid polymer with hydrogen peroxide can not proceed quickly.

3. Organic Peracid Polymer-Containing Composition:

According to the present invention, an organic peracid polymer-containing composition having a high concentration of an organic peracid polymer can be obtained by the above-mentioned producing process. This organic peracid polymer-containing composition is an aqueous solution which at least contains an organic peracid polymer, hydrogen peroxide and an inorganic acid. The concentration of the organic peracid polymer in said composition is 2 to 50% by weight, preferably 2 to 15% by weight. The concentration of hydrogen peroxide is 2 to 50% by weight, preferably 5 to 30% by weight. The concentration of the inorganic acid is 0.1 to 10% by weight, preferably 0.3 to 5% by weight.

When the concentration of the organic peracid polymer is too low, effects as an organic peracid such as disinfectant, bleaching and cleaning effects may not be exhibited sufficiently.

The composition wherein the concentration thereof is too high may be difficult to produce. When the concentration of hydrogen peroxide is too low, the disinfectant, bleaching and cleaning effects may not be exhibited sufficiently. Even if the concentration thereof is too high, said effects may not be improved. When the concentration of an inorganic acid is too low, disinfectant, bleaching and cleaning effects may not be exhibited sufficiently. Even if the concentration thereof is too high, said effects may not be improved.

The above-mentioned organic peracid polymer-containing composition may comprise other optional components including a stabilizer.

According to the organic peracid polymer-containing composition of the present invention, by further diluting the composition containing an organic peracid polymer, hydrogen peroxide and an inorganic acid at the above-mentioned concentration, a diluted composition containing these components at a desired concentration can be provided appropriately.

Examples of diluents include water and an alcoholic aqueous solution. Though its dilution rate is not particularly limited, it is preferable to dilute 1.1 to 10,000 times, more preferably 1.1 to 1000 times.

4. Method for Sterilization, Bleaching and Cleaning:

The disinfectant, bleaching and cleaning composition or the organic peracid polymer-containing composition of the present invention can be used for disinfectant, bleaching and cleaning applications by diluting 1.1 to 10,000 times or without diluting. For example, it can be used for sterilization, bleaching and cleaning of medical devices, beverage or food containers, industrial waste water, cooling water of air conditioners, clothes, cooking devices, dishes, a bathroom, a kitchen, a laundry sink, a bath boiler, furniture and pet animals.

EXAMPLES

Some examples carrying out the present invention will be described below. Note that the following examples do not limit the scope of the present invention.

Examples 1 to 11, Comparative Example 1

Starting materials shown in Table 1 to 2 were mixed together and dissolved at the temperature of 20 to 30° C. Then the transition of aging change of the concentration of the organic peracid polymer and hydrogen peroxide in the composition thus obtained was measured. The charged ratio of the starting materials in each example was shown in Table 1 to 2. The results were shown in Table 3 to 4. In Comparative Example 1, pH was adjusted to 7 by using 0.01 to 1 normal sodium hydroxide.

The method of calculating the concentration of hydrogen peroxide and an organic peracid polymer will be described below: The concentration of hydrogen peroxide was determined by means of titration wherein a permanganic acid potassium salt solution was added to the composition until pink color of permanganic acid does not disappear. Subsequently, the concentration of peroxycarboxyl groups was determined by iodometry. The concentration of an organic peracid polymer was calculated from the concentration of peroxycarboxyl groups based on the structural unit of polymer (—RCOOOH—). For example, in the case of perpolyacrylic acid, it was calculated based on the structural unit of said polymer (—CH$_2$CHCOOOH—, the molecular weight; 88).

To be more precise, it can be calculated by the following calculation formula. In the following calculation formula, P represents the concentration of an organic peracid polymer (% by weight), M represents the molar concentration of peroxycarboxyl groups determined by the above-mentioned titration (mol/l), and W represents [a molecular weight per carboxyl group of polymer+16] respectively.

$$P = M \times W/(1000 \times \text{specific gravity of the composition}) \times 100(\%) \quad \text{(Mathematical Formula 2)}$$

In the examples, "%" means "% by weight". The starting materials used here are as follows. The diluent was water in each case.

(1) Organic Acid Polymer

Polyacrylic acid, Mw5000: manufactured by Wako Pure Chemical Industries, Ltd.
Polyacrylic acid, Mw2000: manufactured by Aldrich.
Polyacrylic acid, trade name "Aqualic HL415", 45% aqueous solution, Mw10000: manufactured by Nippon Shokubai Co., Ltd.
Acrylic acid-maleic acid copolymer, Mw3000, 50% aqueous solution: manufactured by Aldrich.
Polyacrylic acid sodium salt, Mw2700-7500: manufactured by Wako Pure Chemical Industries, Ltd.

(2) Hydrogen Peroxide

Industrial hydrogen peroxide (35%): manufactured by Mitsubishi Gas Chemical Company, Inc.

(3) Inorganic Acid

Sulfuric acid (95.0%): Inujirushi reagent manufactured by Kosou Chemical Co., Ltd.

TABLE 1

| Charged Ratio | Example 1 | Example 2 | Example 3 | Example 4 | Example 5 | Example 6 | Example 7 |
|---|---|---|---|---|---|---|---|
| Organic Acid Polymer, % by weight | 22.3 | 21.9 | 22.0 | 22.3 | 22.3 | 22.3 | 22.3 |
| Hydrogen Peroxide, % by weight | 26.5 | 26.0 | 26.1 | 26.5 | 26.5 | 26.5 | 26.5 |
| Inorganic Acid, % by weight | 1.9 | 3.4 | 1.9 | 2.0 | 1.9 | 1.9 | 1.9 |
| Stabilizer, % by weight | 0 | 0 | 0.96 | 0 | 0.11 | 0.11 | 0.11 |
| Water, % by weight | 49.3 | 48.7 | 49.1 | 49.2 | 49.2 | 49.2 | 49.2 |
| pH | <1.0 | <1.0 | <1.0 | <1.0 | <1.0 | <1.0 | <1.0 |

TABLE 2

| Charged Ratio | Example 8 | Example 9 | Example 10 | Example 11 | Comparative Example 1 |
|---|---|---|---|---|---|
| Organic Acid Polymer, % by weight | 30.0 | 22.4 | 25.3 | 22.3 | 20.4 |
| Hydrogen Peroxide, % by weight | 23.7 | 16.5 | 16.3 | 26.5 | 24.3 |
| Inorganic Acid, % by weight | 2.1 | 2.9 | 2.8 | 1.9 | 0.0 |
| Stabilizer, % by weight | 0 | 0 | 0 | 0 | 0 |
| Water, % by weight | 44.2 | 58.2 | 55.6 | 49.3 | 45.1 |
| Sodium Hydroxide, % by weight | 0 | 0 | 0 | 0 | 10.2 |
| pH | <1.0 | <1.0 | <1.0 | 1.3 | 7.0 |

TABLE 3

| | | Ex. 1 | Ex. 2 | Ex. 3 | Ex. 4 | Ex. 5 | Ex. 6 | Ex. 7 |
|---|---|---|---|---|---|---|---|---|
| Charged Amounts | Polyacrylic acid Mw 5000 | 2 g | 2 g | 2 g | 2 g | 2 g | 2 g | 2 g |
| | Polyacrylic acid Mw 2000 | | | | | | | |
| | Aqualic HL415(45%) Mw 10000 | | | | | | | |
| | Acrylic acid-Maleic acid copolymer(50%)Mw 3000 | | | | | | | |
| | Polyacrylic acid sodium salt Mw 2700-7500 | | | | | | | |
| | Hydrogen Peroxide (35%) | 6 ml | 6 ml | 6 ml | 6 ml | 6 ml | 6 ml | 6 ml |
| | Sulfuric acid | 0.1 ml | 0.1 ml | 0.1 ml | 0.1 ml | 0.1 ml | 0.1 ml | 0.1 ml |
| | Orthophosphoric acid (85%) | | | 0.1 ml | | | | |
| | 1-hydroxyethane-1,1-bisphosphonic acid(60%) | | | | 0.1 ml | | | |
| | Pyrophosphoric acid | | | | | 0.01 g | | |
| | Sodium hexametaphosphate | | | | | | 0.01 g | |
| | Dipicolinic acid | | | | | | 0.01 g | 0.01 g |
| Standing Temperature | | 25° C. | 25° C. | 25° C. | 25° C. | 25° C. | 25° C. | 35° C. |
| Transition Of Ratio | At the time of charging | Concentration of Organic Peracid Polymer (%) | 0.0 | 0.0 | 0.0 | 0.0 | 0.0 | 0.0 | 0.0 |
| | | Concentration of Hydrogen Peroxide (%) | 26.5 | 26.0 | 26.1 | 26.5 | 26.5 | 26.5 | 26.5 |
| | 1 day after | Concentration of Organic Peracid Polymer (%) | 1.7 | 2.0 | 2.0 | 2.0 | 1.9 | 2.1 | 4.8 |
| | | Concentration of Hydrogen Peroxide (%) | 24.9 | 24.5 | 24.7 | 25.1 | 25.1 | 25.2 | 24.6 |

TABLE 3-continued

|  |  | Ex. 1 | Ex. 2 | Ex. 3 | Ex. 4 | Ex. 5 | Ex. 6 | Ex. 7 |
|---|---|---|---|---|---|---|---|---|
| 7 days after | Concentration of Organic Peracid Polymer (%) | 4.5 | 5.5 | 5.6 | 5.5 | 5.6 | 5.8 | 7.2 |
|  | Concentration of Hydrogen Peroxide (%) | 22.7 | 22.7 | 23.4 | 23.5 | 23.4 | 24.4 | 23.5 |
| 15 days after | Concentration of Organic Peracid Polymer (%) | 4.1 | 6.6 | 7.0 | 6.9 | 6.8 | 7.2 | 7.1 |
|  | Concentration of Hydrogen Peroxide (%) | 18.0 | 20.7 | 21.8 | 21.7 | 20.8 | 23.5 | 23.0 |
| 30 days after | Concentration of Organic Peracid Polymer (%) | 3.1 | 5.8 | 6.3 | 6.2 | 6.1 | 7.1 | 6.9 |
|  | Concentration of Hydrogen Peroxide (%) | 7.5 | 15.5 | 18.3 | 18.1 | 16.8 | 22.5 | 21.5 |

TABLE 4

|  |  |  | Ex. 8 | Ex. 9 | Ex. 10 | Ex. 11 | Comparative Ex. 1 |
|---|---|---|---|---|---|---|---|
| Charged Amount | Polyacrylic acid Mw 5000 |  |  |  |  |  | 2 g |
|  | Polyacrylic acid Mw 2000 |  | 2.5 g |  |  |  |  |
|  | Aqualic HL415(45%) Mw 10000 |  |  | 2.5 ml |  |  |  |
|  | Acrylic acid-Maleic acid copolymer(50%)Mw 3000 |  |  |  | 2.5 ml |  |  |
|  | Polyacrylic acid sodium salt Mw 2700-7500 |  |  |  |  | 2 g |  |
|  | Hydrogen Peroxide (35%) |  | 5 ml | 2.5 ml | 2.5 ml | 6 ml | 6 ml |
|  | Sulfuric acid |  | 0.1 ml | 0.1 ml | 0.1 ml | 0.1 ml |  |
|  | Orthophosphoric acid (85%) |  |  |  |  |  |  |
|  | 1-hydroxyethane-1,1-bisphosphonic acid(60%) |  |  |  |  |  |  |
|  | Pyrophosphoric acid |  |  |  |  |  |  |
|  | Sodium hexametaphosphate |  |  |  |  |  |  |
|  | Dipicolinic acid |  |  |  |  |  |  |
| Standing Temperature |  |  | 25° C. | 25° C. | 25° C. | 25° C. | 25° C. |
| Transition Of Ratio | At the time of charging | Concentration of Organic Peracid Polymer (%) | 0.0 | 0.0 | 0.0 | 0.0 | 0.0 |
|  |  | Concentration of Hydrogen Peroxide (%) | 23.7 | 16.5 | 16.3 | 26.5 | 24.3 |
|  | 1 day after | Concentration of Organic Peracid Polymer (%) | 3.3 | 2.4 | 1.8 | 1.8 | 0.0 |
|  |  | Concentration of Hydrogen Peroxide (%) | 22.3 | 15.5 | 15.6 | 25.6 | 16.5 |
|  | 7 days after | Concentration of Organic Peracid Polymer (%) | 3.5 | 3.5 | 3.8 | 2.1 | 0.0 |
|  |  | Concentration of Hydrogen Peroxide (%) | 19.3 | 15.0 | 14.6 | 25.5 | 1.0 |
|  | 15 days after | Concentration of Organic Peracid Polymer (%) | 3.2 | 4.2 | 4.1 | 2.1 | 0.0 |
|  |  | Concentration of Hydrogen Peroxide (%) | 14.8 | 14.4 | 13.9 | 25.5 | 0.2 |
|  | 30 days after | Concentration of Organic Peracid Polymer (%) | 2.7 | 4.0 | 3.4 | 2.0 | 0.0 |
|  |  | Concentration of Hydrogen Peroxide (%) | 9.1 | 13.1 | 13.0 | 25.4 | 0.0 |

In Comparative Example 1, pH was adjusted to 7 by neutralizing with NaOH

Example 12

The composition of 7 days after charging in Example 7 was diluted and the following bleaching test was carried out thereon by using, as a test solution, an organic peracid polymer-containing solution having the effective oxygen concentration of 0.047% wherein pH was adjusted to 7 with 0.01-1N NaOH. The result was shown in Table 5.

The "effective oxygen concentration" here means the theoretical concentration of oxygen released when hydrogen peroxide or an organic peracid polymer is decomposed to be water or an organic acid polymer based upon the total amount of the composition, which is a total of the one derived from hydrogen peroxide and the one derived from the organic peracid polymer. The one derived from hydrogen peroxide can be calculated by "the concentration of hydrogen peroxide×16/34". The one derived from the organic peracid polymer can be calculated by "the concentration of the organic peracid polymer×16/(a molecular weight per carboxyl group of the organic acid polymer+16)". In the case of the composition of 7 days after charging in Example 7, the effective oxygen concentration derived from hydrogen peroxide is 23.5×16/34=11.1%, the effective oxygen concentration derived from the organic peracid polymer is 7.2×16/(72+16)=1.3%, and the effective oxygen concentration in total is 12.4%. In the present experiment, the composition in Example 7 having the effective oxygen concentration of 12.4% is diluted 263 times to obtain an organic peracid polymer-containing solution having the effective oxygen concentration of 0.047.

(Bleaching Test)

Three cuts of contaminated cloth of 5 cm square were immersed in 100 ml of the test solution at the temperature of 25° C. for 30 minutes. Then, they were washed with running water and conducted natural drying. The values of reflectance ratio (457 nm) before and after bleaching were measured by a color-difference meter and a bleaching ratio was determined by the following formula. As the reflectance ratio, an average of 6 values in total for front and back of the three cuts of contaminated cloth was used.

$$\text{Bleaching Ratio}(\%) = ((R_2 - R_1)/(R_0 - R_1)) \times 100$$

$R_0$ represents a reflectance ratio of uncontaminated white cloth, $R_1$ represents a reflectance ratio of contaminated cloth before bleaching and $R_2$ represents a reflectance ratio of contaminated cloth after bleaching. As the contaminated cloth, trade name "EMPA#112" (contaminated cloth with cocoa;

manufactured by EMPA Testmaterials AG in Swiss) and trade name "EMPA#114" (contaminated cloth with red wine; manufactured by EMPA Testmaterials AG in Swiss) were used.

Comparative Example 2

A bleaching test was conducted in the same manner as Example 12, using 0.1% hydrogen peroxide solution wherein pH was adjusted to 7 with 0.01N—NaOH (the effective oxygen concentration of 0.047%). The result was shown in Table 5.

TABLE 5

Results of Bleaching Test (Bleaching Ratio)

| Contaminated cloth | Example 12 | Comparative Example 2 |
|---|---|---|
| EMPA#112 | 11.7% | 5.3% |
| EMPA#114 | 26.0% | 22.8% |

Example 13

The following disinfectant test was carried out by using, as a test solution, an organic peracid polymer-containing solution having the effective oxygen concentration of 1.8% wherein obtained by diluting 6.9 times the composition of 7 days after charging in Example 7 and an organic peracid polymer-containing solution having the effective oxygen concentration of 0.7% obtained by diluting 17.7 times the composition of 7 days after charging in Example 7. The results were shown in Table 6.
(Disinfectant Test)
Test Bacteria Solution (1): *Bacillus subtilis* spore NBRC3134; approximately $10^8$/ml
Test Bacteria Solution (2): *Aspergillus niger* IFO6341; approximately $10^8$/ml
0.05 ml of each bacteria solution was added and mixed with 5 ml of the test solution to operate at the temperature of 20° C. for 30 minutes, and then each 0.1 ml thereof was inoculated into culture media, SCDLP media (soybean-casein digest broth with lecithin and polysorbate 80, manufactured by Nihon Pharmaceutical Co., Ltd.) for (1) and GPLP media (glucose peptone broth with lecithin and polysorbate 80, manufactured by Nihon Pharmaceutical Co., Ltd.) for (2), to incubate. Subsequently, viability test of the bacilli was conducted by evaluation of the presence or absence of opacity in the media.

Comparative Example 3

A disinfectant test was conducted in the same manner as Example 13, using 10.5% hydrogen peroxide solution (the effective oxygen concentration of 4.9%) and 2.1% hydrogen peroxide solution (the effective oxygen concentration of 1.0%). The results were shown in Table 6.

TABLE 6

Results of Disinfectant Test

| | Example 13 | | Comparative Example 3 | |
|---|---|---|---|---|
| Effective Oxygen Concentration (%) | 1.8 | 0.7 | 4.9 | 1.0 |
| Test Bacteria | *Bacillus subtilis* spore | *Aspergillus niger* | *Bacillus subtilis* spore | *Aspergillus niger* |
| Viability | extinct | extinct | survived | survived |

As clear from the results of the above examples, according to the process of mixing an organic acid polymer, hydrogen peroxide and an inorganic acid to provide a composition of the present invention, the concentration of the organic peracid polymer is maximized by keeping for approximately 7 to 30 days after charging and a composition containing high concentration of an organic peracid polymer can be obtained.

In addition, the organic peracid polymer-containing composition of the present invention exhibits remarkably excellent bleaching and disinfectant capabilities compared with a hydrogen peroxide solution having the same effective oxygen concentration.

INDUSTRIAL APPLICABILITY

Since the composition of the present invention contains a sufficient amount of an organic peracid polymer compared with a mere mixture of an organic acid polymer and hydrogen peroxide, it has excellent disinfectant, bleaching and cleaning capabilities, excellent stability, less odor and sufficient water solubility. Therefore, it is excellent in practicality and can be comfortably applied not only for industrial use but also for domestic use.

The composition of the present invention can be used for disinfectant, bleaching and cleaning applications by diluting 1.1 to 10,000 times or without diluting. For example, it can be used for sterilization, bleaching and cleaning of medical devices, beverage or food containers, industrial waste water, cooling water of air conditioners, clothes, cooking devices, dishes, a bathroom, a kitchen, a laundry sink, a bath boiler, furniture and pet animals.

The invention claimed is:

1. A disinfectant, bleaching and cleaning composition which is an aqueous solution consisting essentially of hydrogen peroxide, an inorganic acid, an organic peracid component dissolved in water, and optionally a stabilizer and/or a diluent,
    wherein the organic peracid component consists essentially of an organic peracid polymer selected from the group consisting of perpolyacrylic acid and salts thereof obtained by converting at least part of carboxyl groups in structural units of an organic acid polymer selected from the group consisting of polyacrylic acid and salts thereof into peroxycarboxyl groups.

2. The composition according to claim 1, wherein the converting ratio of carboxyl groups into peroxycarboxyl groups in said organic peracid polymer is not less than 5%.

3. The composition according to claim 1, wherein the molecular weight of said organic peracid polymer is 500 to 100,000.

4. The composition according to claim 1, wherein the concentration of said organic peracid polymer is 2 to 50% by weight.

5. The composition according to claim 1, wherein said inorganic acid is at least one selected from the group consisting of sulfuric acid, orthophosphoric acid and pyrophosphoric acid.

6. The composition according to claim 1, wherein a stabilizer is present.

7. The composition according to claim 6, wherein said stabilizer is at least one selected from the group consisting of orthophosphoric acid, 1-hydroxyethane-1,1-bis(phosphonic acid) or a salt thereof, pyrophosphate, hexametaphosphate and dipicolinic acid.

8. A process for producing an organic peracid polymer-containing composition which is an aqueous solution consisting essentially of hydrogen peroxide, an inorganic acid, an organic peracid component dissolved in water, and optionally a stabilizer and/or a diluent, wherein the organic peracid component consists essentially of an organic peracid polymer selected from the group consisting of perpolyacrylic acid and salts thereof obtained by converting at least part of carboxyl groups in structural units of an organic acid polymer selected from the group consisting of polyacrylic acid and salts thereof into peroxycarboxyl groups, said method comprising at least a mixing step of mixing the following components (i) to (v):
(i) an organic acid polymer selected from the group consisting of polyacrylic acid and salts thereof having carboxyl groups in its structural units,
(ii) hydrogen peroxide,
(iii) an inorganic acid,
(iv) water, and
(v) optionally a stabilizer;
optionally followed by a diluting step, wherein a diluent is added.

9. The process according to claim 8, wherein the mixture is maintained for a period ranging from 1 hour to 1 month in said mixing step.

10. The process according to claim 8, wherein carboxyl groups in the structural units of said organic acid polymer are converted into peroxycarboxyl groups with a converting ratio of not less than 5% in said mixing step.

11. The process according to claim 8, wherein the molecular weight of said organic acid polymer is 500 to 100,000.

12. The process according to claim 8, wherein the mixing ratio of said components (i) to (iv) is 3 to 60% by weight of organic acid polymer, 2 to 60% by weight of hydrogen peroxide, 0.1 to 10% by weight of inorganic acid, and 20 to 90% by weight of water.

13. The process according to claim 8, wherein said inorganic acid is at least one selected from the group consisting of sulfuric acid, orthophosphoric acid and pyrophosphoric acid.

14. The process according to claim 8, wherein a stabilizer is further mixed in said mixing step.

15. The process according to claim 14, wherein said stabilizer is at least one selected from the group consisting of orthophosphoric acid, 1-hydroxyethane-1,1-bis(phosphonic acid) or a salt thereof, pyrophosphate, hexametaphosphate and dipicolinic acid.

16. The process according to claim 8, wherein a diluent is added following the mixing step.

17. An organic peracid polymer-containing composition which is an aqueous solution produced by the process according to any of claims 8-11 or 12-16, which consists essentially of 2 to 50% by weight of the organic peracid polymer, 2 to 50% by weight of hydrogen peroxide, 0.1 to 10% by weight of an inorganic acid, and optionally a stabilizer and/or diluent.

18. An organic peracid polymer-containing diluted composition obtained by diluting the organic peracid polymer-containing composition according to claim 17.

* * * * *